United States Patent
Wise et al.

(10) Patent No.: US 6,264,392 B1
(45) Date of Patent: Jul. 24, 2001

(54) PIVOT JOINT FOR FACESHIELD ASSEMBLY

(75) Inventors: Layton A. Wise, Washington; James R. Tomlinson, Pittsburgh, both of PA (US)

(73) Assignee: Mine Safety Appliances Company, Pittsburgh, PA (US)

( * ) Notice: Subject to any disclaimer, the term of this patent is extended or adjusted under 35 U.S.C. 154(b) by 0 days.

(21) Appl. No.: 09/382,513

(22) Filed: Aug. 25, 1999

(51) Int. Cl.[7] .................................................. A42B 3/22
(52) U.S. Cl. .................. 403/112; 16/542; 2/424; 403/120
(58) Field of Search ............... 16/342, 334; 403/112, 403/94, 95, 120; 296/97.1; 2/424, 10

(56) References Cited

U.S. PATENT DOCUMENTS

| | | |
|---|---|---|
| 4,109,320 | 8/1978 | Anderson . |
| 4,479,738 | 10/1984 | Kubrick . |
| 5,008,976 * | 4/1991 | Busch .................................. 16/342 X |
| 5,185,889 * | 2/1993 | Kamata ................................... 2/424 |
| 5,987,651 * | 11/1999 | Tanaka ..................................... 2/424 |
| B1 6,182,330 * | 2/2001 | Novin et al. ....................... 16/334 X |

FOREIGN PATENT DOCUMENTS

| | | |
|---|---|---|
| 36 30 516A | 3/1988 | (DE) . |
| 94 01 066 U | 3/1994 | (DE) . |

OTHER PUBLICATIONS

Patent Abstracts of Japan vol. 1995, No. 11, Dec. 26, 1995 & JP 07216622A (Koken KK) Aug. 15, 1995.

* cited by examiner

Primary Examiner—Lynne H. Browne
Assistant Examiner—John R. Cottingham
(74) Attorney, Agent, or Firm—James G. Uber; Douglas Hanscom

(57) ABSTRACT

A faceshield that is securable to a protective helmet or headband having an indexable pivot joint which utilizes an interference fit between an O-ring and radially spaced lug sets. The O-ring is compressed when the crests of the two sets of lugs are radially aligned. This interference holds the faceshield in a desired indexed position.

20 Claims, 3 Drawing Sheets

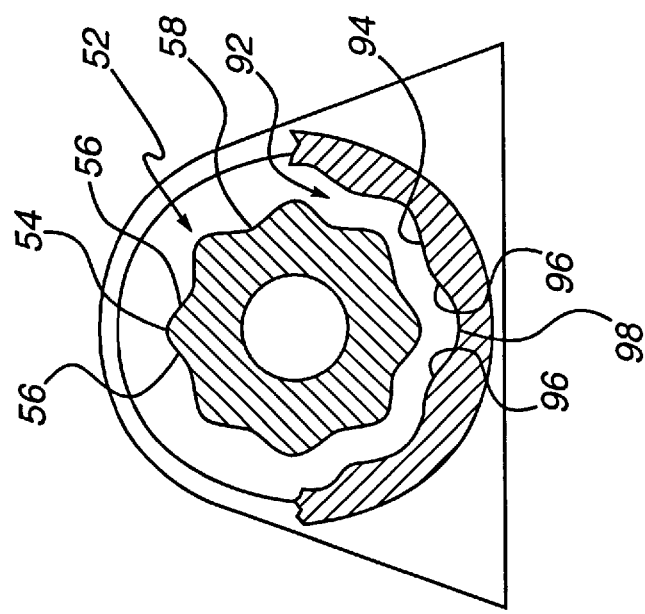
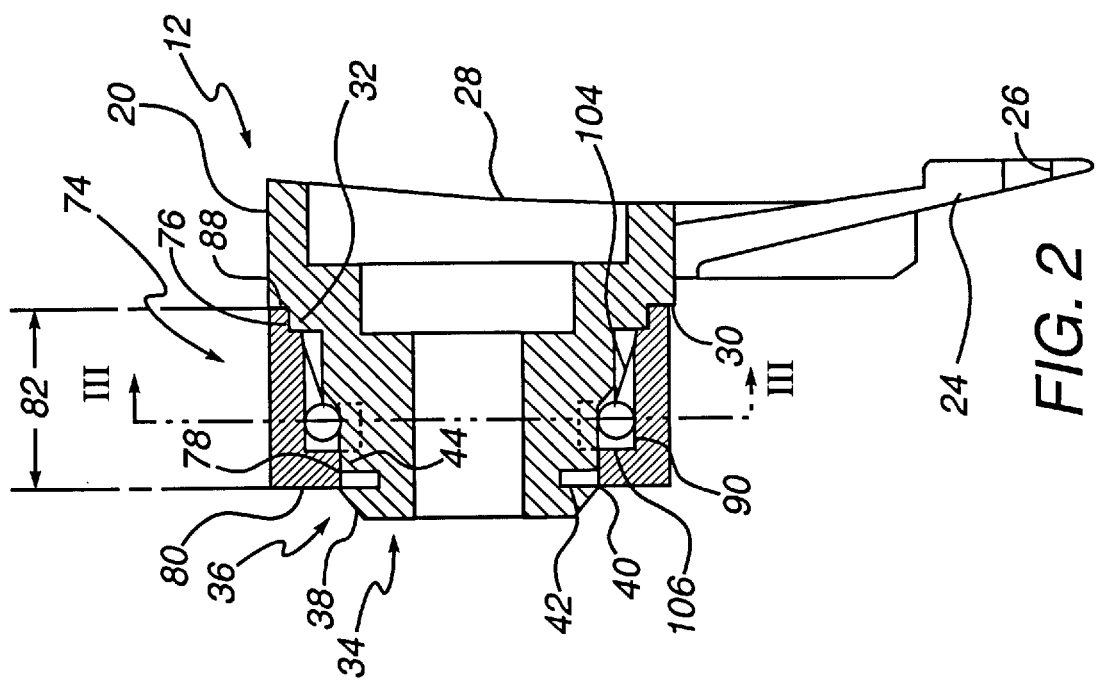

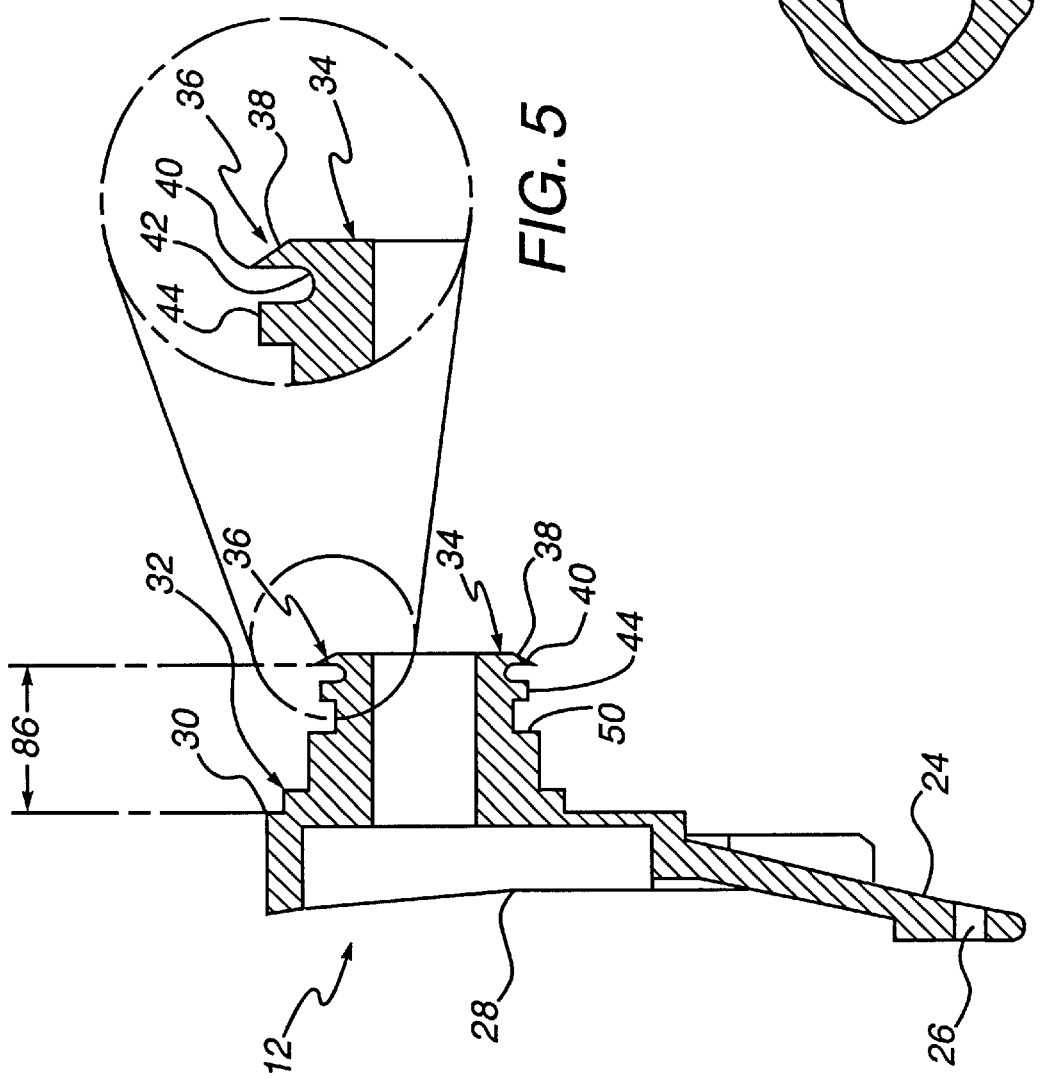
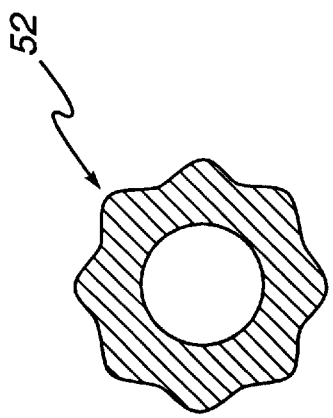

PIVOT JOINT FOR FACESHIELD ASSEMBLY

FIELD OF THE INVENTION

The present invention is directed generally to a pivot joint for a faceshield assembly. More particularly, the present invention is directed to an indexing pivot joint for a faceshield. Most specifically, the present invention is directed to a multi-positional indexing pivot joint for a faceshield assembly.

BACKGROUND OF THE INVENTION

Faceshield assemblies are an integral component of protective equipment worn by personnel in any number of industrial settings. Such faceshields may cover only the wearer's eyes or may be full face and chin covering shields. These faceshields are typically worn by workers in environments where an eye or face hazard is present such as welding or grinding. The faceshields may be attached to protective helmets or may be attached to headbands or the like. While such faceshields are intended to be placed in a down or use position while the wearer is in the hazardous environment, they are typically also moveable to an up or non-use position when the wearer leaves the hazardous situation. It is therefore important that the faceshield be attached to its supporting headgear in a manner which will facilitate deployment between use and non-use positions.

Various attachments and joints for use in securing faceshields to their associated headgear are known. These have sometimes taken the form of a threaded stud on the bracket, an aperture on the visor arm or faceshield arm that fits over the stud, and a separate knob which engages the threaded stud. Upon tightening of the knobs on each side of the faceshield, the shield can be held in a desired position. Another known pivot joint for a faceshield can utilize a ratchet and pawl arrangement. The bracket can be provided with a resilient pawl that will engage any one of a plurality of ratchet teeth on the faceshield arms. Pin and detent arrangements, spring and ball assemblies, plain friction joints, and other similar arrangements are also provided in the field for use in providing an indexing or multiple position holding capability for a faceshield.

These currently available structures for attaching a faceshield to a piece of headgear suffer from a variety of problems and limitations. These render the assemblies difficult to use and expensive to manufacture. Any number of faceshield assemblies will provide protection for the wearer, if he or she will wear them. If the faceshield assembly is not easy to use, if it does not stay in an up or down position, or a desired intermediate position or, if it cannot easily be repositioned, the faceshield may not be used. The best faceshield assembly will do no good if its operation is SO difficult or inconvenient that the user chooses not to wear it.

Unfortunately, many of the known faceshield repositioning joint assemblies have limitations. For example, the faceshield either will not stay up, will not stay in its intended use position but instead rests against the face of the wearer, or requires two hands and too much time to change positions. The threaded stud and knob arrangement requires two hands, the ratchet and pawl assembly can break, the pin and detent wears out, and the friction joint slips.

It is desirable, therefore, to provide a pivot joint for a faceshield assembly which overcomes the limitations of the known devices. Such a pivot joint is provided by the present invention which is a substantial improvement over these devices.

SUMMARY OF THE INVENTION

Generally, the present invention provides an indexing pivot joint for a faceshield assembly. Preferably, the present invention provides a multi-position indexing pivot joint for a faceshield assembly. The faceshield is supported by a visor arm which attaches, at its ends, to brackets which may be integral with, or which may be affixable to a protective helmet or a piece of headgear, such as a headband. Lugged surfaces on both the visor arm ends and the brackets engage intermediate O-rings which provides the indexing position capability of the pivot joint.

Preferably, the present invention provides a pivot joint for a faceshield assembly which has few moving parts and thus can be manufactured at a low cost, is dependable, and has a long life.

As will be discussed in greater detail in the description of the preferred embodiment which is set forth subsequently, the pivot joint for faceshield assemblies in accordance with the present invention utilizes lugs formed on the inner peripheral surface of visor arm or faceshield end sleeves in cooperation with lugs on the exterior circumferential surface of a bracket post or stud, together with an interposed O-ring. The visor or faceshield arm end sleeves snap fit over the outer ends of the respective bracket posts or studs which support them. The lugs on the arms and the lugs on the post or stud are never in physical contact with each other. Instead, they both engage the O-ring which is concentric with both and held between the two sets of lugs. When a lug crest on each member is radially aligned with a lug valley on the other member, there is little force exerted on the O-ring. When the lug crests on both members are radially aligned, the O-ring interposed between the two is compressed to a sufficient amount that the faceshield will stay in its indexed position. A greater or fewer number of lugs can be provided on each or both of the arm end sleeves and the bracket studs or posts, in accordance with the desired number of indexed positions in which to place the faceshield assembly. Even one lug is enough as long as there are several lugs on the opposing member. Additionally, the lug crest heights can either be uniform or non-uniform. If the crest heights are non-uniform, the higher crests will provide a more stable indexed position while the lower crest or crests will provide a more easily released indexed position.

The pivot joint for faceshield assemblies in accordance with the present invention overcomes the limitations of the known devices. For example, the faceshield can be easily shifted between its various indexed positions using only one hand since there are no threaded knobs or the like to be loosened and no small balls to depress or detents to disengage. There is nothing required of the user except his light grasp of the faceshield with one hand and his movement of the faceshield to its desired position.

From a manufacturing standpoint, the pivot joint of the present invention is not complicated and can be easily adapted to a number of faceshield and visor arm structures and to various brackets for attaching to a protective helmet. The visor arm sleeve ends snap fit over the bracket posts and are supported by two spaced bearing surfaces for long life and smooth operation. The resilient O-ring is long wearing and desirable. The two components have a low profile and a minimal diameter so that they do not appreciably increase the size or the bulk of either the visor arm ends or the bracket.

The pivot joint for faceshield assemblies in accordance with the present invention overcomes many limitations of the known devices. It is a substantial advance which will ensure that the faceshield or protective visor with which it is incorporated is comfortable and easy to use and therefore worn by the person who is to be protected. Other details and advantages of the present invention will become apparent as the following description of the invention proceeds.

BRIEF DESCRIPTION OF THE DRAWINGS

In the accompanying drawings, preferred embodiments of the invention and preferred methods of practicing the invention are illustrated in which:

FIG. 2 is a cross-sectional view of an assembled pivot joint;

FIG. 3 is an end view, partly in section and with the O-ring removed, of the pivot joint, taken along line III—III of FIG. 2;

FIG. 4 is a cross-sectional side elevation view of the bracket portion of the pivot joint;

FIG. 5 is an enlarged view of the encircled position of FIG. 4;

FIG. 6 is a cross-sectional view of the bracket post and showing a regular lug pattern; and FIG. 7 is a cross-section view of the bracket post and showing an irregular lug pattern.

DESCRIPTION OF THE PREFERRED EMBODIMENT

Figure 1:
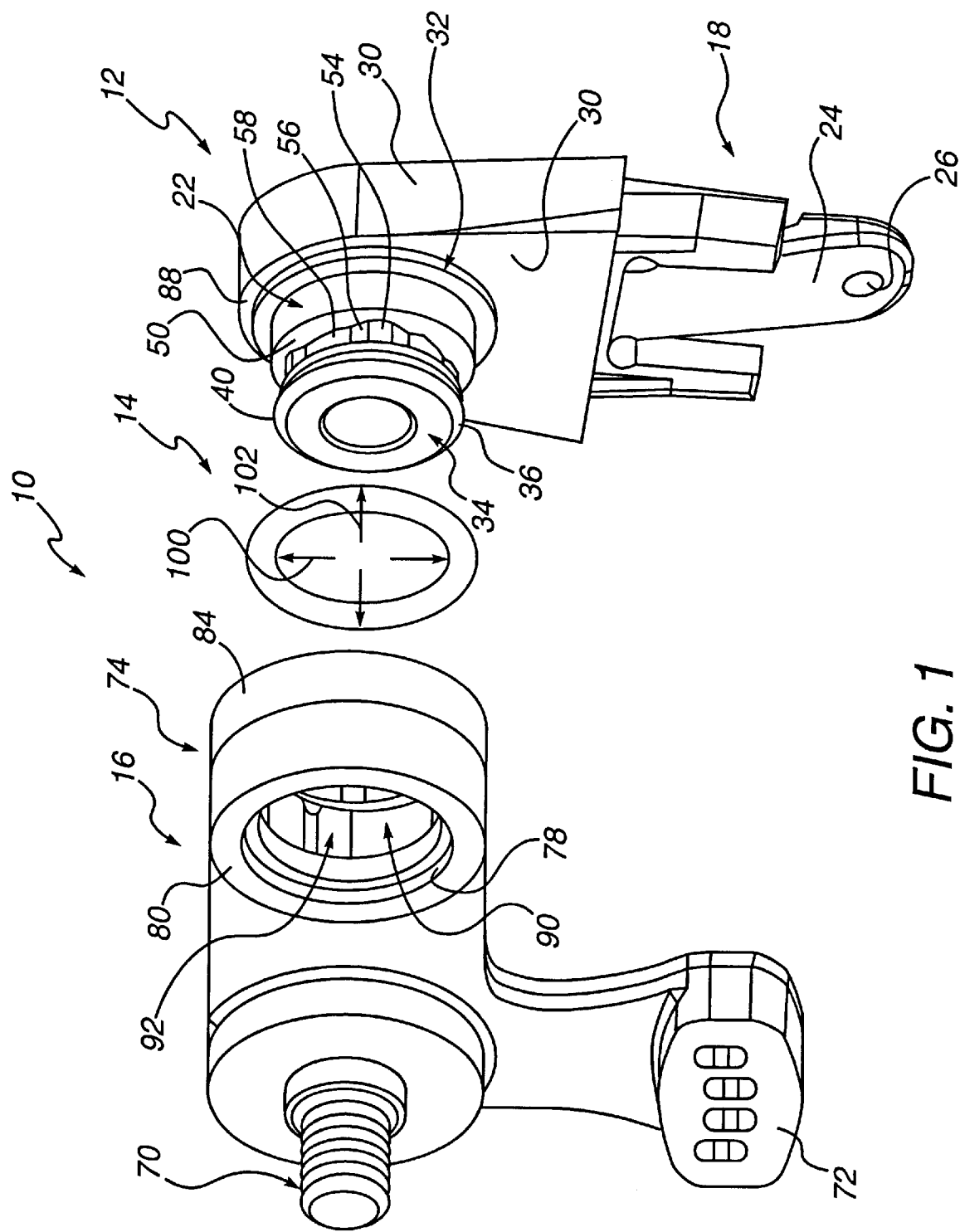
FIG. 1 is an exploded perspective view of a pivot joint for a faceshield assembly in accordance with the present invention.

Turning initially to FIG. 1, there may be seen generally at 10 a preferred embodiment of a pivot joint for a faceshield assembly in accordance with the present invention. Pivot joint assembly 10 is assembled from three components, a bracket 12, an O-ring 14, and a visor arm 16. Each of the bracket 12 and the visor arm 16 are illustrated in FIG. 1 in one of a variety of possible configurations. For example, bracket 12 is depicted as a separate element which could either be attached directly to a protective helmet or which could be attached to a separate headband. The bracket could alternatively, be molded as an integral part of a protective helmet, an attaching bracket, or a separate headband. In a similar fashion, the visor arm depicted in FIG. 1 is structured to receive one or more styles of faceshields. It is readily apparent that a number of different overall visor arms could be used in a faceshield assembly having a pivot joint of the present invention. While the following discussion will be directed to one preferred bracket structure and to one preferred visor arm structure, the subject invention is not limited to any one such overall structure.

Again referring to FIG. 1, the bracket 12 is preferably formed from a single piece of material such as DELRIN™ or another suitable plastic. Bracket 12 preferably includes a bracket mounting plate 18, a bracket post support 20, and a bracket post 22. The bracket mounting plate 18 has a connector such as tongue 24 which can snap-fit into a cooperating shaped socket on a protective helmet (not shown). The tongue 24 is also provided with an aperture 26 which could receive a chin strap. The bracket post support 20 is formed integral with the bracket mounting plate 18 and is shaped to have a low profile so that it will be flat against the side of a protective helmet. As may be seen in FIGS. 2 and 4, the rear surface 28 of the bracket post support 20 is somewhat concave so that it will snugly engage the side of a protective helmet. Alternatively, bracket post support 20 may form part of a headband or head encircling strap.

Bracket post 22 is, as may be seen in FIGS. 1 and 4, a generally cylindrical member and is joined at an inner end to a front surface 30 of the bracket post support 20 by an inner arm support bushing 32. At its outboard end 34 the bracket post 22 is formed with a tapered flange 36 which can be seen more clearly in FIGS. 2 and 4. This flange 36 has an inclined flange face 38 which terminates in a flange lip 40. The flange lip 40 has a diameter which is slightly greater than a diameter of a sleeve portion of the visor arm, as will be discussed in greater detail shortly. An annular groove 42 is formed just inboard of the flange lip 40 on the bracket post 20. This annular groove 42 separates the flange lip 40 from an outer visor arm support bushing 44, again as may be seen most clearly in FIG. 5.

A bracket post channel 50 is formed in the bracket post 22 intermediate the post's inner arm support bushing 32 and outer arm support bushing 44. Bracket post channel 50 has an inner surface which is defined by a plurality of regularly spaced bracket post lugs 52. These lugs may be seen most clearly in FIG. 3. Each such bracket post lug has a lug crest 54 and lug sidewalls 56. The individual bracket post lugs 52 are evenly spaced about the surface of the bracket post is channel 50 and are separated by bracket lug valleys 58. This regular pattern of similarly shaped bracket post lugs 52 may also be seen quite clearly in FIG. 6. An alternate arrangement of bracket post lugs is shown in FIG. 7. In this alternate configuration, some of the lugs are designated as major lugs 60 while others are designated as minor lugs 62. These major and minor bracket post lugs 60 and 62, respectively, can be arranged in an alternating pattern spaced radially from each other at 45 degrees, as shown in FIG. 7. Other patterns of major and minor lugs 60 and 62, whose function will be discussed in detail in a subsequent section, are also possible. In all configurations of the bracket post lug arrangement, the crest 54 of the highest lugs define a bracket post crest diameter which is no greater than, and which is preferably less than, the diameter of the bracket post intermediate the inner and outer bracket arm support bushing surfaces 32 and 44.

Returning again to FIG. 1, the pivot joint for a faceshield assembly, generally at 10 further includes the visor arm shown generally at 16. As was indicated previously, the visor arm 16 shown in FIG. 1 is to be understood as being exemplary of a variety of visor arm configurations which are useable with the present invention. In this visor arm, a threaded stud 70 and a multiapertured pad 72 are formed to receive any one of a number of welding faceshields, all of which are generally conventional and do not form a part of the present invention. These faceshields are not shown but it will be understood that it is the purpose of the pivot joint of the present invention to facilitate the attachment of faceshields and similar protective face gear to a protective helmet or to a headband that can be placed on a wearer's head or secured to a protective helmet. The visor arm is formed with a visor arm sleeve 74 which is sized to be slid over the bracket post 22. To facilitate this placement, the visor arm sleeve 74 has an inner stepped sleeve journal 76 which, as seen in FIG. 2, is of a diameter and shape to ride on and to be supported by the inner stepped arm support bushing 32 of the bracket post 22. An outer sleeve journal 78 is located in the visor arm sleeve 74 adjacent an outer sleeve face 80. When the visor sleeve 74 is slid onto the bracket post 22, the outer sleeve journal 78 is supported by, and rides on the outer visor arm sleeve support bushing 44, all as may be seen most clearly in FIG. 2.

The outer visor sleeve journal has an inner diameter which is slightly less than the diameter of the flange lip 40.

Since the flange 36 as well as the rest of the bracket post 22 are made using a somewhat resilient plastic material, the flange lip 40 will deflect slightly as the visor sleeve 74 is slid onto the bracket post 22. The length 82 of the visor sleeve from its outer face 80 to a visor sleeve inner stop face 84 is slightly less than a bracket post length 86 from the flange lip 40 to a bracket post inner abutment 88 that is defined by the vertical wall surface of the front surface 30 of the bracket post support 20 adjacent the inner arm sleeve support bushing 32. The result of this structural cooperation is that once the visor arm sleeve 74 has been slid onto the bracket post 22, the flange lip 40 will snap back into place to effectively lock the sleeve 74 onto the post 22. The resiliency and flex of the flange lip 40 is enhanced by the provision of the annular groove 42 just inboard of the flange lip 40 on the bracket post 22.

Again referring to FIG. 1 and as also may be seen in FIG. 3, the inner surface of the visor arm sleeve 74, intermediate the inner stepped sleeve journal 76 and the outer sleeve journal 78, is provided with a sleeve lug channel 90. This sleeve lug channel carries a plurality of spaced visor arm sleeve lugs 92 which are seen in FIG. 1, and which may also be seen in FIG. 3. The sleeve lugs 92 are evenly spaced about the sleeve lug channel 90. Each sleeve lug 92 has a sleeve lug crest 94 and sleeve lug sidewalls 96, as shown in FIG. 3. The sleeve lugs are separated by sleeve lug valleys 98. Preferably, all of the sleeve lugs have the same crest height and the visor sleeve lug crests define sleeve lug crest diameter.

The sleeve lug crest diameter is always greater than the bracket lug crest diameter which was discussed previously. As may be seen by referring to FIG. 3, there is always a radially extending space maintained between the bracket post lug crests and the visor arm sleeve lug crests when the bracket and arm are assembled, as seen in FIG. 2. The lugs 52 and 92 are concentric, with the sleeve lugs 92 overlying the bracket lugs 52. It is to be clearly understood, however, that these two sets of lugs do not intermesh as would the teeth on a pair of cooperating gear sets. Instead, the resilient O-ring 14 is interposed between the crest sets 52 and 92 when the visor arm sleeve 74 is slid over the bracket post 22. This O-ring is made of any suitable resilient material. It has an O-ring inner diameter 100 that is slightly smaller than the bracket post lug crest diameter. An outer diameter 102 of the O-ring 14 is slightly greater than the visor arm sleeve lug crest diameter. The thickness of the O-ring 14 is greater than the distance between the post crest diameter and the sleeve crest diameter. It is the interference between the O-ring 14 and the post lug crests 54 and the sleeve lug crests 94 that provides the indexing capability of the pivot joint of the present invention.

As the visor arm sleeve 74 is slid over the bracket post 22, after the O-ring 14 has been placed in the bracket post channel 50, the O-ring 14 will be held between the two sets of lugs 52 and 92. The sleeve lugs 92 have inclined ramp leading surfaces 104, as seen in FIG. 2, so that the O-ring 14 will not be rolled out of the bracket post channel 50. An upstanding wall 106 at the outboard end of the sleeve lug channel 90 also serves to hold the O-ring 14 in place. As was discussed previously, the flange lip 40 acts to hold the visor arm sleeve 74 in place on the bracket post 22 with the sleeve being supported for rotation on the post by the cooperation of the inner sleeve support bushing 32 with the inner stepped sleeve journal 76, and the outer visor arm sleeve support bushing 44 with the outer sleeve journal 78.

Although the O-ring 14 is not shown in FIG. 3, it will be understood that the O-ring is interposed between the post lugs 52 and the sleeve lugs 92. With the post lugs 52 and the sleeve lugs 92 arranged out of phase, as seen in FIG. 3, i.e., with the post lug crests 54 radially aligned with the sleeve lug valleys 98, the O-ring 14 will be in a complementary, generally sinusoidal configuration. If the visor arm sleeve 74 is rotated with respect to the bracket post 22, the sleeve lug crests 94 will move to a position where they are radially aligned with the post lug crests 54. In this alignment position of the two lugs sets, the O-ring 14 will be pinched or compressed between each of the pairs of radially aligned crests of the two lug sets. This interference of the O-ring 14 with the crests 54 and 94 will hold the visor arm 16 in the desired indexed position. The number of such indexed positions will be understood as being a function of the number of circumferentially spaced lugs 52 and 92 whose crests 54 and 94 can be aligned.

It will be recalled that a bracket post lug arrangement of major lugs 60 and minor lugs 62 was discussed in connection with FIG. 7. The radial spacing between even the minor lugs 62 of the bracket post lugs 52 and the lugs 92 of the visor arm sleeve is still less than the thickness of the O-ring 14 but is greater than the spacing between the major lugs 60 and the lugs 92. In such a configuration, the indexed position of the visor arm 16 with respect to the bracket post 12 is less stable when the minor lugs 62 are radially aligned with the sleeve lugs 92. Such a variable indexing strength may be desirable in certain applications. For instance, if the faceshield attached to the visor arm 16 is being used by a welder, it may be desirable to have a major indexed position of the faceshield in a full up position or a full down position; i.e., visor horizontal or visor vertical. However, it may also be desirable to have a minor indexed position; i.e. visor at 45' with the visor being capable of being returned to the full down indexed position merely by having the wearer nod his head. The lug arrangement of FIG. 7 will accomplish this.

The pivot joint for a faceshield assembly in accordance with the present invention provides for a number of indexing positions and strengths to be selected. The number of lugs in each of the two lug sets can be varied. The resiliency of the O-ring, as well as its thickness, can be changed. The use of major and minor lugs will accommodate the need for varying amounts of faceshield stability in each of the selected indexed positions. The selection of suitable materials for the bracket, the sleeve and the O-ring will provide smooth, long-lived operation with a minimal likelihood of malfunction.

While preferred embodiments of a pivot joint for faceshield assemblies in accordance with the present invention have been set forth fully and completely hereinabove, it will be understood that a number of changes in, for example, the type of faceshield being used, the structure of the protective helmet and the like, could be made without departing from the true spirit and scope of the present invention which is limited only by the following claims.

What is claimed is:

1. A pivot joint assembly comprising:
 a bracket having a bracket post;
 a plurality of bracket lugs formed on an outer surface of the bracket post;
 a support arm having a support arm sleeve, the sleeve being adapted to overlie and to be concentric with the bracket post;
 a plurality of sleeve lugs on an inner surface of the sleeve and concentric with the bracket lugs; and
 a ring of resilient material interposed between and interferingly engaging the bracket lugs and the sleeve lugs.

2. The pivot joint assembly of claim 1 wherein the bracket post includes a bracket post channel and further wherein the bracket lugs are positioned in the bracket post channel.

3. The pivot joint assembly of claim 1 wherein the sleeve includes a sleeve lug channel and further wherein the sleeve lugs are positioned in the sleeve lug channel.

4. The pivot joint assembly of claim 1 wherein the bracket includes a bracket mounting plate and a bracket post support, the bracket post being joined to the bracket post support.

5. The pivot joint assembly of claim 4 further including a connector on the bracket mounting plate useable to secure the bracket to a protective helmet.

6. The pivot joint assembly of claim 1 further including a visor arm on the support arm, the visor arm adapted to support a faceshield.

7. The pivot joint assembly of claim 1 wherein the bracket lugs include bracket lug crests and the sleeve lugs include sleeve lug crests, the bracket lug crests and the sleeve lug crests being radially alignable and having a crest spacing distance when radially aligned and further wherein the ring of resilient material has a thickness which is greater than the crest spacing distance.

8. The pivot joint assembly of claim 1 further including an inner sleeve support bushing and an outer sleeve support bushing on the bracket post, and an inner sleeve journal and an outer sleeve journal on the support arm sleeve, the inner and outer sleeve support bushings supporting the inner and outer sleeve journals when the sleeve overlies the bracket post.

9. The pivot joint assembly of claim 1 further including a tapered flange at a free end of the bracket post and a resilient flange lip on the tapered flange.

10. The pivot joint assembly of claim 9 further including an outer sleeve face on the support arm sleeve, the outer sleeve face being in snap-fit engagement with the resilient flange lip when the support arm sleeve overlies the bracket post.

11. The pivot joint assembly of claim 1 wherein the plurality of bracket lugs include major lugs and minor lugs.

12. The pivot joint assembly of claim 1 further including tapered leading edge ramp surfaces on the sleeve lugs.

13. The pivot joint assembly of claim 1 wherein the O-ring is made of rubber.

14. The pivot joint assembly of claim 1 wherein there are eight sleeve lugs and eight bracket lugs.

15. The pivot joint assembly of claim 1 wherein there are eight sleeve lugs and four bracket lugs.

16. The pivot joint assembly of claim 1 wherein the support arm supports a faceshield.

17. The pivot joint assembly of claim 7 wherein the bracket lug crests are not uniform in height.

18. The pivot joint assembly of claim 1 wherein the ring of resilient material is an O-ring.

19. A pivot joint assembly comprising:
   a bracket having a bracket post;
   a plurality of bracket lugs formed on an outer surface of the bracket post;
   a support arm having a support arm sleeve, the sleeve being adapted to overlie and to be concentric with the bracket post;
   a sleeve lug on an inner surface of the sleeve and concentric with the bracket lugs; and
   a ring of resilient material interposed between and interferingly engaging the bracket lugs and the sleeve lug.

20. A pivot joint assembly comprising:
   a bracket having a bracket post;
   a bracket lug formed on an outer surface of the bracket post;
   a support arm having a support arm sleeve, the sleeve being adapted to overlie and to be concentric with the bracket post;
   a plurality of sleeve lugs on an inner surface of the sleeve and concentric with the bracket lug; and
   a ring of resilient material interposed between and interferingly engaging the bracket lug and the sleeve lugs.

* * * * *